July 12. 1932. J. H. JAMES Re. 18,522
INTERMEDIATE PARTIAL OXIDATION PRODUCT AND METHOD OF MAKING SAME
Original Filed Jan. 22, 1919
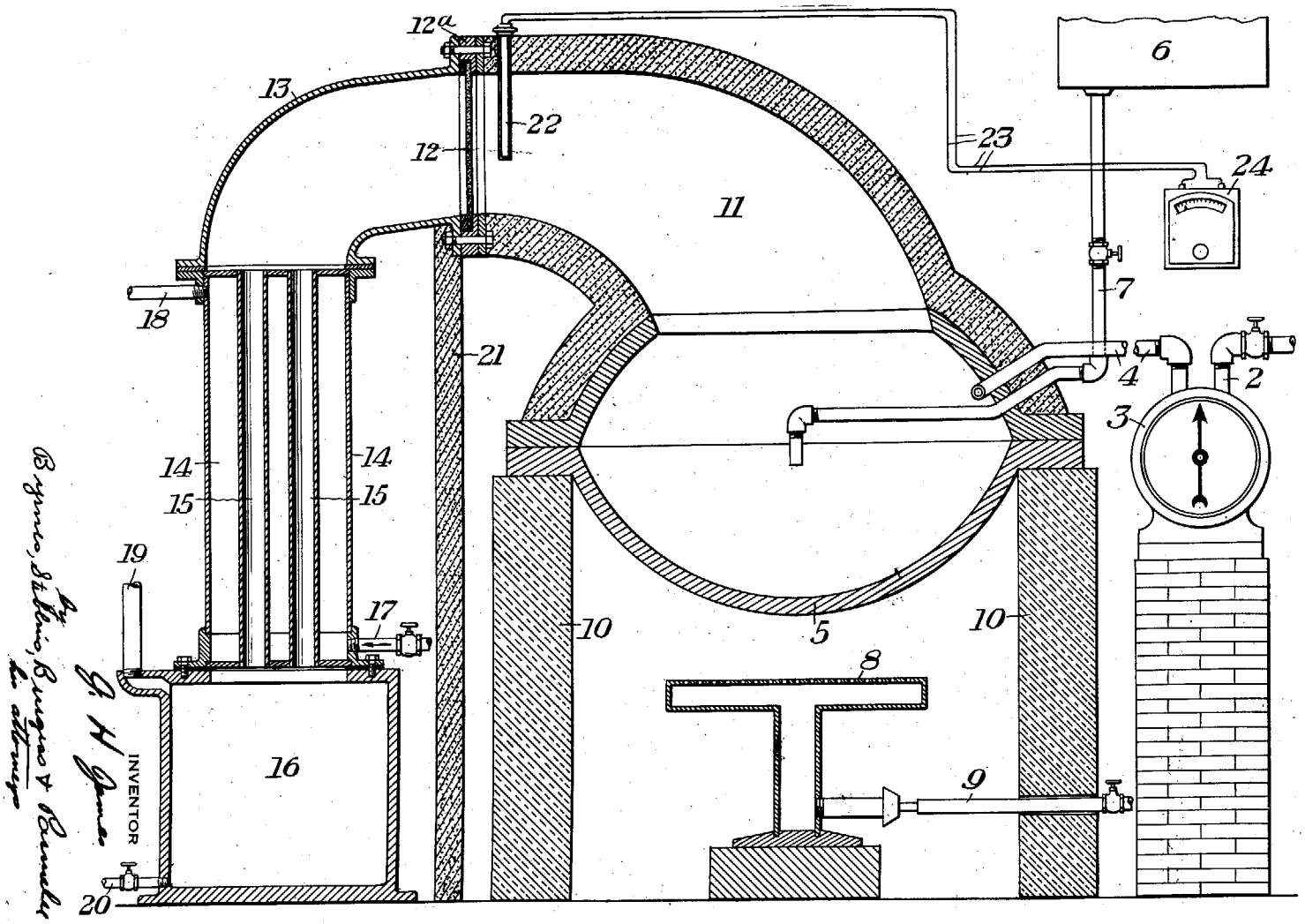
INVENTOR
J. H. James
By Byrnes, Stebbins, Burgess & Barnes
his attorneys Reissued July 12, 1932 Re. 18,522

UNITED STATES PATENT OFFICE

JOSEPH HIDY JAMES, OF PITTSBURGH, PENNSYLVANIA, ASSIGNOR TO CLARENCE P. BYRNES, TRUSTEE, OF SEWICKLEY, PENNSYLVANIA

INTERMEDIATE PARTIAL OXIDATION PRODUCTS AND METHOD OF MAKING SAME

Original No. 1,697,653, dated January 1, 1929, Serial No. 281,124, filed March 7, 1919. Renewed August 4, 1926. Continuation of application Serial No. 272,567, filed January 22, 1919. Application for reissue filed May 21, 1932. Serial No. 612,838.

The figure is a sectional side elevation, showing one form of apparatus for carrying out my invention.

My invention relates to a partial oxidation product and method of making the same, and forms a continuation of my copending application, Serial No. 272,567, filed January 22, 1919, which was a continuation in part of my then pending application, Serial No. 132,569, filed November 21, 1916. In those applications I disclosed a liquid partial oxidation product having a plurality of different hydrocarbons containing artificially-introduced chemically-combined oxygen. I also disclosed a partial oxidation process wherein a mixture of carbon-hydrogen-oxygen containing constituents in gaseous phase, and more particularly a hydrocarbon-oxygen mixture in gaseous phase, was passed in contact with a catalyst at an elevated temperature below that of continuous self-sustained combustion, and preferably below a red heat. The hydrocarbon employed was preferably a mineral oil, such as one of the distillates of petroleum, although the process might be applied to crude oil or oils from shales or their distillates, or oils from low temperature distillation of lignites or coals, or other distillates. I disclosed the vaporizing of such oils, forming a heated mixture of the oil vapor with a measured proportion of air, either with or without steam, and passing the heated mixture in contact with a suitable catalyst while keeping the reaction below that of continuous self-sustained combustion, thereby producing a mixture of valuable intermediate oxidation products in the range from alcohol to oxygenated organic acids, and could hold the reaction temperature within the proper range by maintaining proper conditions.

In such process, while heat is continuously supplied to vaporize the oil, and, if necessary, additional heat is supplied to bring the mixture to the reacting temperature, especially in starting; yet the catalyst is kept below a red heat and preferably below a heat which shows any glow, to prevent continuous self-sustained combustion which would consume a large amount of the hydrocarbon. The heat might rise temporarily to a point of ignition, but in such case the yield is reduced; and the air and vapor ratio should be changed to prevent a continuance of such combustion.

If steam is added, it will serve as a diluent to hold down the reaction zone temperature, and will also aid in vaporizing heavier oils. The amount of steam should be carefully regulated.

By long experimenting I have found that a number of inter-depending variable conditions or factors dependent on each other are important in obtaining proper yields. Thus, the proportion of air, the particular catalyst used, the velocity of the current or steam, and the temperature maintained in the reaction zone are inter-dependent and should be accordingly varied in relation to each other. The thickness of catalyst is also a factor. The air ratio should be maintained preferably above the theoretical amount to give the desired intermediate oxidation products, but below that for complete combustion; and at such a rate that continuous self-sustained combustion does not occur. The reaction gives out heat and the temperature should be held down in the conversion zone. The variable factors may be inter-adjusted to give a product wherein other intermediate oxidation products predominate over any organic acids produced, and the hydrocarbon may be mixed with oxygen or an oxygen-containing gas in forming the gaseous phase mixture. In making a predominance of bodies other than acids, the temperature is preferably somewhat lower than where a larger percentage of acids is desired.

The range of temperature for carrying out my invention extends, so far as I have determined, from about 230° C. up to 450°–500° C. The temperature used will depend somewhat upon the particular hydrocarbon being treated, from gasoline to the heaviest hydrocarbons that can be vaporized; and also depends somewhat on the particular catalyst used, the proportion of air or oxygen employed, whether or not steam is added, and to some extent, on the speed of the current or steam mixture. I have found that the lighter the hydrocarbon treated, the higher the reaction zone temperature should be maintained; and accordingly, when heavier distillates are used, lower temperatures may be employed.

The catalysts hereinafter described differ in activity. With an active catalyst kept at the highest temperature consistent with a high commercial yield, the proportion of air may be kept at or above that required by theory for the products desired, the temperature, of course, being kept below that where products of complete combustion, namely, carbonic dioxide and water, form to a large extent. With more active catalysts a higher speed may be used, especially where a higher temperature within the desirable range is employed. The time of contact with the catalyst may be lessened when a more active catalyst and a higher temperature are used. With hydrocarbons of greater molecular weight more heat must be applied to vaporize them, but the reaction zone heat should be lower than otherwise. With hydrocarbons of less molecular weight, less heat will vaporize them, but the temperature of the reaction zone should be higher within the desirable range. With fractions of widely different molecular weight the difference in reaction zone temperature is rather marked.

The desired temperature in the reaction zone can be kept down below a glowing temperature by lowering the proportion of air nearer the theoretical amount as the temperature rises, and by raising the proportion of air as the temperature decreases, within certain limits.

The products after leaving the reaction zone are either cooled and condensed, or absorbed for recovery.

The catalyst, when used, is preferably arranged in a layer or succession of layers, and preferably consists of the oxides or compounds of metals having more than one valence, such, for example, as blue oxides of molybdenum or the oxides of vanadium or uranium.

The products of this method are condensed by reducing the temperature of the outlet gases and products, and also preferably by bringing them in contact with a liquid such as water, giving mixtures of partial oxidation products usually ranging from alcohols through aldehydes to aldehyde fatty acids.

The process can be varied by varying the factors of temperature, proportions of mixture, speed of flow, amount of diluent, etc., to either give a preponderance of products short of acids or a preponderance of acids. The present divisional case is intended to cover the new product wherein the other intermediate oxidation products preponderate over the acids, as well as that form of the method which produces such a product.

For example, by keeping the reaction zone temperature below a red heat and below that which produces a preponderance of acids, I can produce in commercial quantities a mixture of valuable oxidation products, including aldehydes and alcohols, and can hold the reaction temperature within the preferred range by regulating the external heat applied for vaporizing the liquid hydrocarbon or hydrocarbon derivative when in liquid form, or otherwise maintaining proper conditions.

If steam is added it will serve as a diluent to hold down the reaction zone temperature and will also aid in vaporizing heavier hydrocarbons. The steam should be carefully regulated and when properly used will aid in increasing the yield. The proportion of air, the particular catalyst used, the temperature maintained, and other factors are inter-dependent and should be accordingly varied in proper relation to each other under the conditions of each material treated and the products desired. Heat may be continuously supplied to vaporize the oil, and the air ratio is preferably maintained somewhat above the theoretical amount for the products desired. The reaction gives out heat and the temperature should be held down in the conversion zone.

As regards the catalyst, I prefer to employ the complex oxides or compounds of metals having a varying valence. All parts of the complex may consist of oxides of the same metal or of different metals. For example, an excellent catalyst in this connection consists of the blue oxides of molybdenum which contain molybdenyl-molybdenate and molybdenyl-molybdenite, and are probably all chemical compounds of two or more oxides of molybdenum representing different states of oxidation. These complexes may be regarded as salts, i. e., compounds of one or more basic oxides with one or more acid oxides. Other complexes of value for such catalysts are chromic chromate, tungsten tungstate, the manganese complexes, the vanadium complexes, etc.

The basic and acid parts of these complexes may be formed from oxides of different metals, in which case each metal or group of metals used should possess varying valence. Examples, of this class are: uranyl molybdate, uranyl molybdite, cobalt molybdate, cobalt molybdite, uranyl vanadate, uranyl vanadite, etc.

The metals, whose oxide complexes I prefer to employ as the acid part of the catalyst, since I have found them to be of high activity in this field, are the metals of high melting point electronegative low-atomic-volume metals having an atomic weight above 40. These metals appear on the Lothar Meyer diagram of the periodic series beginning on the descending side of the third peak, descending side of the fourth peak and the descending side of further peaks developed since the date of this diagram. The class includes the following metals: titanium, vanadium, chromium, manganese, zirconium, niobium, molybdenum, tantalum, tungsten and uranium. The basic oxides may be the lower oxides of these metals or may be the oxides, of iron, copper, nickel, lanthanum, cobalt, thorium, and the eight or nine rare earth metals.

In both acid or basic portions there may, of course, be two or more of these combined. The conditions will vary somewhat, depending upon the particular catalyst employed. Some catalysts tend to produce more acids and other catalysts tend to produce more intermediate oxidation products short of acids.

With the above description of the conditions, which are varied in order to give the best commercial results according to the interaction of the factors described, I will now describe one form of apparatus for carrying out my invention.

In the drawing, 2 represents a valved air pipe through which air is supplied under pressure, 3 a meter for the air, and 4 the pipe leading from the meter into a heating and mixing vessel 5. 6 represents a vessel containing liquid hydrocarbon and 7 a valved pipe leading therefrom into the mixing vessel 5. 8 indicates a burner having a valved supply pipe 9, by which the heat may be regulated. 10 represents the walls of the furnace or heating chamber in which the retort or mixing vessel 5 is set, the heated mixture of hydrocarbon vapor and air passing from the mixing vessel through the channel 11 to the catalytic screen 12. This catalytic screen is shown as having a frame 12[a], clamped or bolted between the ends of the channel 11 and the flanged end of the conduit 13, leading to a vertical condenser 14. The products emerging from the catalytic screen pass down through the tubes 15 of the condenser into the vessel 16. 17 represents the valved inlet pipe for water passing into the condenser, and 18 the outlet pipe for the circulating water. The vessel 16 is provided with an outlet 19 for fumes, 20 being the valved pipe by which the condenser products are drawn off. Between the condenser and the vessel 16 and the furnace I preferably provide an insulating screen 21 of some heat insulator to keep the heat of the furnace away from the condensing apparatus.

22 represents a pyrometer which is preferably in the form of an electric couple with its wires 23 leading to an external temperature indicator 24.

As the heated mixture of vapor and air in the proper proportions passes through the catalytic screen under the regulated temperature referred to, partial oxidation or partial combustion takes place, the products being immediately taken to and through the condenser, and the desired product collecting in the vessel succeeding the condenser. The condensing apparatus may, of course, be of any desirable type, either in single or multiple form. I may in some cases lead pipe 19 to a scrubbing system to recover any uncondensed products.

I will now describe some specific examples of my process.

(1) Using as a catalyst "blue oxides" of molybdenum, the coated asbestos layer being 1 centimeter thick and 4.4 centimeter diameter. The oil used was a gas oil fraction distilling from 250 to 295 degrees C. The air rate was two liters per minute or 1.6 times the theoretical amount required for aldehyde fatty acid formation. The absorbers consisted of eight water bubblers. The oil was fed at the rate of 126 cubic centimeters per hour. The time of contact with the catalyst was .32 seconds; the temperature of the catalyst was maintained at about 270 degrees C.; the duration of the run was one hour and 35 minutes. A test of the exit gas showed 2.4% of carbon dioxide and 1% of oxygen. 150 cubic centimeters of liquid oxidation products were recovered, of which about 45% by volume consisted of oxygenated organic acids and about 55% of other products in the range from alcohols to acids, including unchanged hydrocarbons.

(2) The catalyst consisted of uranyl uranate and uranyl uranite on asbestos 1.25 centimeters thick and 4.4 centimeters in diameter. The oil used was kerosene distilling at 250 to 295° C. The air rate was 4 liters per minute, the condensing and absorbing system consisting of two worm condensers and four water bubblers. The oil was fed in at the rate of 200 cubic centimeters per hour. The time of contact was about .33 second. The temperature of the catalyst was maintained at about 310° C. The duration of the run was 33 minutes. As a result, 76 cubic centimeters of liquid product were recovered, which, on analysis, gave about 70% of aldehydes (aldehyde-like bodies) and about 30% of aldehyde fatty acids, there being some alcohols present.

With an apparatus for larger scale operation, practically identical with the drawing accompanying this specification, the following run was made:

*Conditions*

(*a*) Catalyst: "blue oxides" of molybdenum on asbestos, held between parallel wire mesh screens as shown in figure, the active material, packed in the disk-shaped space 15 inches in diameter and 2/5 of an inch thick.

(*b*) Hydrocarbon mixture treated: "mineral seal oil", a Pennsylvania pertroleum distillate, 90% of which distilled between 250 and 324 degrees C. The distillate had a specific gravity of .8125 at 20 degrees C.

(*c*) Air rate: about 216 cubic feet per hour.

(*d*) Absorbing system: no scrubbers, only the parallel tube condenser as shown in figure.

(*e*) Oil feed: 2.5 gallons per hour.

(*f*) Time of contact of h. c. vapor-air mixture with catalyst: approximately .3 second.

(*g*) Temperature of catalyst: 310 to 320 degrees C.

(*h*) Total time consumed in run: 2 hours.

*Results*

(*a*) Carbon dioxide analysis (by volume) in exit gas stream during run: (6%, 1.0%, .8%).

Carbon monoxide analysis (by volume) in exit gas stream during run: (6.8% 8.%).

(*b*) 3.7 gallons of product (having specific gravity at 20 degrees C. of .852) were recovered which had the following analysis: aldehyde fatty acids, 46% by volume, aldehyde 28%, leaving undetermined 26% by volume.

Actual recovery of aldehyde acids, by weight, based on weight of hydrocarbon mixture treated: 50.7%.

The above examples in connection with the description of the apparatus and operation will sufficiently disclose to those skilled in chemistry the essentials of the process, under the conditions recited above.

So far as I have found, the lowest reacting temperature for successful commercial operation can be used when the catalyzer consists of the intermediate complex compounds of oxides of molybdenum. The next lowest temperature has been used with a catalyst consisting of the compounds of molybdenum with other metallic oxides of the group above named.

A catalytic layer is important in producing commercial yields, although a non-catalytic screen may be used, or even a plain tube to surround the reaction zone, with lower percentages of yield.

The resulting material containing partial oxidation products short of acids and of different molecular weights may be used in the industries, or the product, or a part thereof, may be further oxidized; as, for example, by again passing it through the process.

I have also obtained a preponderance of bodies short of acids, including aldehyde-like bodies, using the blue oxides of molybdenum as a catalyst, and a temperature of about 230 to 250° C., the air rate being about 1.6 times the theoretical amount required for producing such products.

By the words "mineral hydrocarbons" in the claims I intend to include crude mineral oil or shale oil, or their distillates, products or derivatives including hydrocarbon gas whether "wet" or "dry", or the products or derivatives from low temperature distillation of lignites or coals. The oils or distillates, or products thereof, may vary, some having a paraffin base and some having an asphaltum base. Such oils contain saturated straight chain or branched chain aliphatic hydrocarbons, and may also contain unsaturated straight chain or branched chain hydrocarbons, such as those of the olefin type and those of the acetylene type. They may also contain some aromatic or other cyclic hydrocarbons with side chains, the latter being saturated or unsaturated, and also naphthenes.

Many changes may be made in the material treated in the apparatus, the various conditions, etc., without departing from my invention, since I consider myself the first to discover a practicable process whereby hydrocarbons may be converted by vapor or gas phase partial oxidation into a product having a preponderance of partial oxidation products short of acids.

By the terms "aldehyde fatty acids" and "aldehyde acids" herein, I intend to include such forms of oxygenated organic acids as are produced by my partial oxidation methods from hydrocarbons or hydrocarbon products or derivatives in the form of gases or liquids, and the exact character and form of which are not now fully known.

The claims herein are intended to cover my broad partial oxidation process and product and also the species where the oxidation products short of acids predominate, as well as the species where acids predominate. My application Ser. No. 272,567 will contain claims to certain other features not herein claimed.

I claim:

1. As a new article of manufacture, a liquid partial oxidation product containing organic acids of the fatty acid type and a material proportion of intermediate oxidation products, the oxidation products short of aldehyde fatty acids being in excess of said acids.

2. As a new article of manufacture, a liquid partial oxidation product containing organic acids of the fatty acid type and a material proportion of intermediate oxidation products, the oxidation products short of aldehyde fatty acids being of different molecular weights and being in excess of said acids.

3. As a new article of manufacture, a liquid gaseous phase partial oxidation product containing a material proportion of aliphatic aldehydes of different molecular weights the oxidized bodies short of organic acids being in predominance.

4. As a new article of manufacture, a liquid partial oxidation product containing aldehyde-like bodies and aldehyde fatty acids, the former being in excess of the latter.

5. As a new article of manufacture, a liquid partial oxidation product containing a material proportion of aliphatic intermediate oxidation products, those products short of acids being in excess of any organic acids.

6. As a new article of manufacture, a liquid partial oxidation product containing aliphatic aldehydes, aldehyde fatty acids and unconverted hydrocarbons, the aldehydes and unconverted hydrocarbons being in excess of the aldehyde fatty acids.

7. As a new article of manufacture, a liquid gaseous phase partial oxidation product containing a plurality of aliphatic aldehyde-like bodies in material proportion, the oxidized bodies short of organic acids being in predominance.

8. The process of making aldehyde-like bodies, consisting in passing a heated mixture of mineral hydrocarbon and air through a hot reaction zone, and maintaining the zone temperature and the air ratio below that of continuous self-sustained combustion and below that at which aldehyde acids predominate.

9. In the process of making aliphatic aldehydes, the steps consisting of passing a mixture of finely divided hydrocarbons and air through a hot reaction zone at a temperature below red heat and within the range where the aldehydes in the product predominate over the acids produced.

10. In the process of making aliphatic aldehyde-like bodies, the steps consisting in passing a heated mixture of hydrocarbon vapor and air over a catalyst containing a compound of a metal of high-melting-point electronegative low-atomic volume at a temperature below red heat and within the range where the aldehyde-like bodies in the product predominate over aldehyde fatty acids.

11. In the manufacture of a liquid partial oxidation product having a plurality of different hydrocarbons containing artificially-introduced chemically-combined oxygen, the steps consisting of forming a gaseous-phase mixture of aliphatic hydrocarbon and oxygen, passing the mixture over a catalyst at a temperature below a red heat, and interadjusting the variable factors in the range where other intermediate oxidation products predominate over any acids produced.

12. In the manufacture of a liquid partial oxidation product having a plurality of different hydrocarbons containing artificially-introduced chemically-combined oxygen, the steps consisting of forming a gaseous-phase mixture of aliphatic hydrocarbon and oxygen, passing the mixture through a hot reaction zone at a temperature below a red heat, and interadjusting the variable factors in the range where other intermediate oxidation products predominate over any acids produced.

13. In the manufacture of a liquid partial oxidation product having a plurality of different hydrocarbons containing artificially-introduced chemically-combined oxygen, the steps consisting of forming a gaseous-phase mixture of hydrocarbon and oxygen, passing the mixture over a catalyst at a temperature below a red heat and in the range where other intermediate oxidation products predominate over any acids produced.

14. In the manufacture of a liquid partial oxidation product having a plurality of different hydrocarbons containing artificially-introduced chemically-combined oxygen, the steps consisting of forming a gaseous-phase mixture of aliphatic hydrocarbon and oxygen, passing the mixture over a catalyst containing a compound of a metal of high melting point electro-negative low-atomic volume at a temperature below a red heat, and interadjusting the variable factors in the range where other intermediate oxidation products predominate over any acids produced.

15. In the manufacture of a liquid partial oxidation product having a plurality of different hydrocarbons containing artificially-introduced chemically-combined oxygen, the steps consisting of forming a gaseous-phase mixture of aliphatic hydrocarbon and oxygen, passing the mixture over a catalyst at a temperature below a red heat, and maintaining the temperature and the oxygen ratio below that of continuous self-sustained combustion and within the range wherein other intermediate oxidation products predominate over any acids produced.

16. The process of synthetically forming an aliphatic liquid partial oxidation product containing a predominance of intermediate oxidation products short of acids, consisting of passing a mixture of carbon-hydrogen-oxygen containing constituents in gaseous phase in contact with a catalyst at an elevated temperature below a red heat and at a pressure less than 5 atmospheres.

17. The process of synthetically forming an aliphatic liquid partial oxidation product containing a predominance of intermediate oxidation products short of acids, consisting of passing a mixture of carbon-hydrogen-oxygen containing constituents in gaseous phase in contact with a catalyst containing compounds of at least two different groups of the periodic series other than the alkali metal group.

18. The process of synthetically forming an aliphatic liquid partial oxidation product containing a predominance of intermediate oxidation products short of acids, consisting of passing a mixture of carbon-hydrogen-oxygen containing constituents in gaseous phase in contact with a catalyst containing compounds of at least two different groups of the periodic series other than the alkali metal group at an elevated temperature below a red heat and at a pressure less than 5 atmospheres.

19. In the manufacture of a partial oxidation product containing a predominance of intermediate oxidation products short of acids, the steps consisting of forming a gaseous-phase mixture of hydrocarbon and oxygen, passing the mixture over a catalyst at a temperature below that of continuous self-sustained combustion, and interadjusting the variable factors to produce unconsumed oxygen in the tail gas and give a product wherein other intermediate oxidation products predominate over any acids produced.

20. In the manufacture of a partial oxidation product containing a predominance of intermediate oxidation products short of acids, the steps consisting of forming a gaseous-phase mixture of aliphatic hydrocarbon and oxygen, passing the mixture over a catalyst at a temperature below that of continuous self-sustained combustion, interadjusting the variable factors in the range wherein other intermediate oxidation products predominate over any acids produced, and collecting water soluble products in a water solution.

21. In the process of synthetically forming an aliphatic liquid partial oxidation product containing a predominance of intermediate oxidation products other than acids, the steps consisting of passing a mixture of carbon-hydrogen-oxygen containing constituents in gaseous phase in contact with a catalyst containing compounds of a plurality of metals, one of which belongs to the high-melting-point electronegative low-atomic-volume class.

22. In the process of synthetically forming an aliphatic liquid partial oxidation product containing a predominance of intermediate oxidation products other than acids, the steps consisting of passing a mixture of carbon-hydrogen-oxygen containing constituents in gaseous phase in contact with a catalyst containing compounds of a plurality of metals, two of which belong to the high-melting-point electronegative low-atomic-volume class.

23. In the process of synthetically forming a liquid partial oxidation product containing a predominance of intermediate oxidation products other than acids, the steps consisting of passing a mixture of aliphatic hydrocarbon and oxygen containing constituents in gaseous phase in contact with a catalyst containing compounds of a plurality of metals, one of which belongs to the high-melting-point electronegative low-atomic-volume class.

24. In the process of synthetically forming a liquid partial oxidation product containing a predominance of intermediate oxidation products other than acids, the steps consisting of passing a mixture of aliphatic hydrocarbon and oxygen containing constituents in gaseous phase in contact with a catalyst containing compounds of a plurality of metals, two of which belong to the high-melting-point electronegative low-atomic volume class.

25. In the process of synthetically forming a liquid partial oxidation product containing a predominance of intermediate oxidation products other than acids, the steps consisting of passing a mixture of aliphatic hydrocarbon and oxygen containing constituents in gaseous phase in contact with a catalyst containing compounds of a plurality of metals, one of which belongs to the high-melting-point electronegative low-atomic volume class, at an elevated temperature below a red heat.

26. In the process of synthetically forming an aliphatic liquid partial oxidation product containing a predominance of intermediate oxidation products other than acids, the steps consisting of passing a mixture of carbon-hydrogen-oxygen containing constituents in gaseous phase in contact with a catalyst containing compounds of a plurality of metals, one of which belongs to the high-melting-point electronegative low-atomic-volume class, and condensing the products both indirectly and by direct contact with a liquid.

27. In the process of synthetically forming an aliphatic liquid partial oxidation product containing a predominance of intermediate oxidation products other than acids, the steps consisting of passing a mixture of hydrocarbon and oxygen containing constituents in gaseous phase in contact with a catalyst containing compounds of a plurality of metals, one of which belongs to the high-melting-point electronegative low-atomic volume class, and condensing the products both indirectly and by direct contact with a liquid.

28. In the process of making intermediate oxidation products containing a predominance of products other than acids, the steps consisting of passing a gaseous mixture of aliphatic hydrocarbon and oxygen containing constituents through a hot reaction zone at a temperature below that of continuous self-sustained combustion and interadjusting the variable factors to give a product wherein other intermediate oxidation products predominate over any acids produced.

29. In the process of making intermediate oxidation products containing a predominance of products other than acids, the steps consisting of passing a gaseous mixture of aliphatic hydrocarbon and oxygen containing constituents through a hot reaction zone at a temperature below that of continuous self-sustained combustion and interadjusting the variable factors to produce unconsumed oxygen in the tail gas and give a product wherein other intermediate oxidation products predominate over any acids produced.

30. In the process of making partial oxidation products by partial combustion the steps consisting of passing a mixture of mineral oil vapor and air through a catalyst and maintaining the reaction temperature below that of continuous self-sustained combustion.

31. In the process of making partial oxidation products by partial combustion, the steps consisting of mixing hot mineral oil vapor with air, passing the mixture through a catalyst and maintaining the catalyst at a temperature below a red heat.

32. In the process of making partial combustion products, the steps consisting in passing a gaseous phase mixture of aliphatic hydrocarbon and oxygen-containing gas through a catalyst at a temperature below that of continuous self-sustained combustion and within the partial combustion range.

33. In the process of making partial combustion products, the steps consisting of mixing finely divided mineral oil with air in measured amounts, passing the mixture in contact with a catalyst and maintaining the catalyst at a temperature below a red heat.

34. In the process of making partial combustion products, the steps consisting of vaporizing mineral oil by applying external heat to a vessel containing the oil, mixing oxygen and a diluent in measured amounts with the hot vapor, and passing the preheated mixture through a heated conversion zone at a temperature below red heat and within the intermediate oxidation range for the mixture used.

35. In the process of making partial combustion products, the steps consisting of vaporizing mineral oil by applying external heat to a vessel containing the oil, mixing oxygen and a diluent in measured amounts with the hot vapor and passing the mixture through a catalyst, and maintaining the catalyst at a temperature below a red heat.

36. In the process of making partial combustion products, the steps consisting of vaporizing mineral oil by applying external heat to a vessel containing the oil, mixing oxygen and a diluent in measured amounts with the hot vapor and passing the mixture through a catalyst, and maintaining the catalyst at a temperature below a red heat by regulating the amount of external heat applied for vaporizing the oil.

37. In the process of making partial combustion products, the steps consisting of passing a heated mixture of mineral oil vapor and air through a hot reaction zone and maintaining the zone temperature and the air ratio below that of continuous self-sustained combustion and within the intermediate oxidation range for the mixture used.

38. In the process of making partial combustion products, the steps consisting of feeding mineral oil to a container, applying external heat to the container to vaporize the oil, feeding regulated amounts of air, forming a heated mixture of the oil vapor and air, passing the heated mixture through a catalyst, indicating the temperature of the catalytic zone, and regulating said catalytic zone temperature.

39. In the process of making partial combustion products, the steps consisting of feeding mineral oil, applying external heat and continuously vaporizing the oil, feeding regulated amounts of air, forming a heated mixture of the oil vapor and air, passing the heated mixture through a catalyst, indicating the temperature of the catalytic zone, and regulating said catalytic zone temperature by regulating the amount of external heat applied in vaporizing the oil.

40. In the process of making partial combustion products, the steps consisting of passing a mixture of mineral oil vapor and air through a catalyst at a temperature below a red heat.

41. In the process of making partial combustion products, the steps consisting of passing a mixture of heated mineral oil vapor, air and a diluent through a hot reaction zone at a temperature below red heat.

42. In the process of making partial combustion products, the steps consisting of passing a mixture of mineral oil vapor and air through a heated reaction zone at a temperature between 230° C. and about 450° C., and condensing and recovering a material percentage of intermediate combustion products.

43. In the process of making partial combustion products, the steps consisting in passing a mixture of mineral oil vapor, air and a diluent through a heated reaction zone at a maintained temperature of between 230° C. and 450° C., and condensing and recovering a material percentage of intermediate combustion products.

44. In the process of making partial combustion products, the steps consisting of passing a heated mixture of mineral oil vapor and air through a catalyst containing a compound of a metal of high melting point, electro-negative low-atomic volume at a temperature below that of continuous self-sustained combustion.

45. In the process of making partial combustion products, the steps consisting in passing a mixture of mineral oil vapor and air through a catalyst containing the complex compounds of metal of electronegative low-atomic volume having a varying valence at a temperature below that of continuous self-sustained combustion.

46. In the process of making partial combustion products, the steps consisting of mixing finely divided mineral oil with air in measured amounts, passing the mixture in contact with a catalyst, and maintaining the catalyst at a temperature below a red heat and within the range where aldehyde fatty acids predominate over aldehydes in the product.

47. As a new article of manufacture, a liquid gaseous-phase partial oxidation product containing a material proportion of aliphatic aldehydes of different molecular weights.

48. As a new article of manufacture, a liquid gaseous-phase partial oxidation product containing a plurality of aliphatic aldehyde-like bodies in a material proportion.

49. As a new article of manufacture, a liquid gaseous-phase partial oxidation product containing a material proportion of aliphatic aldehydes and aldehyde fatty acids.

50. In the process of catalytic oxidation of petroleum hydrocarbons the step which comprises passing the reaction mixture of petroleum vapor and air over a catalytic mass maintained at a black heat just below a low red heat.

51. In the catalytic oxidation of petroleum oils the step which comprises passing a mixture of petroleum vapor and air over a composite catalyst containing two active oxidizing agents maintained at a black heat approaching red heat.

52. In the manufacture of a liquid partial oxidation product, the steps consisting of forming a gaseous-phase mixture of aliphatic hydrocarbon and oxygen and passing the mixture through a hot reaction zone at a temperature below that of continuous self-sustained combustion.

53. In the manufacture of a liquid partial oxidation product, the steps consisting of forming a gaseous phase mixture of aliphatic hydrocarbon and oxygen and passing the mixture through a hot reaction zone at a temperature below a red heat.

54. In the manufacture of liquid partial oxidation products the steps consisting of forming a gaseous-phase mixture of aliphatic hydrocarbon and oxygen and passing the mixture over a catalyst at a temperature below that of continuous self-sustained combustion.

55. In the manufacture of liquid partial oxidation products the steps consisting of forming a gaseous-phase mixture of aliphatic hydrocarbon and oxygen and passing the mixture over a catalyst at a temperature below a red heat.

56. In the manufacture of liquid partial oxidation products the steps consisting of forming a gaseous-phase mixture of aliphatic hydrocarbon and oxygen and passing the mixture over a catalyst containing a compound of a high melting point electronegative low-atomic-volume metal at a temperature below that of continuous self-sustained combustion.

57. In the process of making oxygenated organic acids, the steps consisting in passing a mixture of heated mineral oil vapor and air through a catalyst at a reactive temperature below that of continuous self-sustained combustion and within the partial combustion range and interadjusting the variable factors to produce a predominance of organic acids.

58. In the process of making oxygenated organic acids, the steps consisting of mixing finely divided mineral oil with air in measured amounts, passing the mixture in contact with a catalyst, maintaining the catalyst at a reactive temperature below a red heat and interadjusting the variable factors to produce a predominance of organic acids.

59. In the process of making oxygenated organic acids, the steps consisting of vaporizing mineral oil by applying external heat to a vessel containing the oil, mixing oxygen and a diluent in measured amounts with the hot vapor, passing the mixture through a catalyst, maintaining the catalyst at a reactive temperature below that of continuous self-sustained complete combustion by regulating the amount of external heat applied for vaporizing the oil and interadjusting the factors to produce a predominance of organic acids.

60. In the process of making oxygenated organic acids, the steps consisting of passing a heated mixture of mineral oil vapor and air through a hot reaction zone, maintaining the reactive zone temperature and the air ratio below that of continuous self-sustained combustion and within the intermediate oxidation range for the mixture used and within the range for producing a predominance of organic acids.

61. In the process of making oxygenated organic acids, the steps consisting of feeding mineral oil to a container, applying external heat to the container to vaporize the oil, feeding regulated amounts of air, forming a heated mixture of the oil vapor and air, passing the heated mixture through a catalyst, maintaining the catalyst at a reactive temperature, indicating the temperature of the catalytic zone, and regulating said catalytic zone temperature to produce a predominance of organic acids.

62. In the process of making oxygenated organic acids, the steps consisting of feeding mineral oil, applying external heat and continuously vaporizing the oil, feeding regulated amounts of air, forming a heated mixture of the oil vapor and air, passing the heated mixture through a catalyst, indicating the temperature of the catalytic zone, and regulating said catalytic zone temperature by regulating the amount of external heat applied in vaporizing the oil to produce a predominance of organic acids.

63. In the process of making oxygenated organic acids, the steps consisting of passing a mixture of mineral oil vapor and air through a catalyst at a reactive temperature below a red heat, and interadjusting the variable factors to produce a predominance of organic acids.

64. In the process of making oxygenated organic acids, the steps consisting of passing a mixture of heated mineral oil vapor, air and a diluent through a hot reaction zone at a reactive temperature below that of continuous self-sustained complete combustion and interadjusting the factors to produce a predominance of organic acids.

65. In the process of making oxygenated organic acids, the steps consisting of passing a mixture of mineral oil vapor and air through a heated reaction zone at a temperature between 230° C. and about 450° C., and interadjusting the factors to produce a predominance of organic acids.

66. In the process of making oxygenated organic acids, the steps consisting in passing a mixture of mineral oil vapor, air and a diluent through a heated reaction zone at a maintained temperature of between 230° C. and about 450° C., and interadjusting the factors to produce a predominance of organic acids.

67. In the process of making oxygenated organic acids, the steps consisting of passing a heated mixture of mineral oil vapor and air through a catalyst containing a compound of a metal of high melting point, electro-negative low-atomic volume at a reactive temperature below that of continuous self-sustained combustion, and interadjusting the factors to produce a predominance of acids.

68. In the process of making oxygenated organic acids, the steps consisting in passing a mixture of mineral oil vapor and air through a catalyst containing the complex compounds or metal of electronegative low-atomic volume having a varying valence at a reactive temperature below that of continuous self-sustained complete combustion, and interadjusting the variable factors to produce a predominance of organic acids.

69. In the process of making partial combustion products, the steps consisting of mixing finely divided mineral oil with air in measured amounts, passing the mixture in contact with a catalyst, maintaining the catalyst at a reactive temperature below a red heat and interadjusting the proportions of the mixture and the temperature to give at least twenty percent of aldehyde fatty acids in the product.

70. In the process of catalytic oxidation of petroleum hydrocarbons, the steps which comprise passing the reaction mixture of petroleum vapor and air over a catalytic mass maintained at a black heat just below a low red heat and interadjusting the variable factors to produce a predominance of organic acids.

71. In the catalytic oxidation of petroleum oils, the steps which comprise passing a mixture of petroleum vapor and air over a composite catalyst containing two active oxidizing agents maintained at a black heat approaching red heat and interadjusting the variable factors to produce a predominance of organic acids.

72. In the process of treating petroleum products, the steps which comprise mixing said products with a gas containing oxygen in amount less than that required for complete combustion, and passing said mixture at a reactive temperature through a reaction zone at a rate which leaves unconsumed oxygen in the product.

73. In the manufacture of oxygen derivatives of hydrocarbon, the steps consisting of forming a gaseous-phase mixture of hydrocarbon and oxygen and passing the mixture through a hot reaction zone at a reactive temperature below that of continuous self-sustained complete combustion, and interadjusting the variable factors to produce unconsumed oxygen in the tail gas and a predominance of organic acids.

74. In the manufacture of liquid partial oxidation products, the steps consisting of forming a gaseous-phase mixture of hydrocarbon and oxygen and passing the mixture over a catalyst at a reactive temperature below that of continuous self-sustained complete combustion and interadjusting the variable factors to produce unconsumed oxygen in the tail gas and a predominance of organic acids.

75. In the manufacture of oxygenated organic acids, the steps consisting of passing a mixture of carbon-hydrogen-oxygen containing constituents in gaseous phase at a reactive temperature in contact with a catalyst containing compounds of a plurality of metals, one of which belongs to the high-melting-point electronegative low-atomic-volume class and interadjusting the variable factors to produce a predominance of organic acids.

76. In the manufacture of oxygenated organic acids, the steps consisting of passing a mixture of carbon-hydrogen-oxygen containing constituents in gaseous phase at a reactive temperature in contact with a catalyst containing compounds of a plurality of metals, two of which belong to the high-melting-point electronegative low-atomic-volume class and interadjusting the variable factors to produce a predominance of organic acids.

77. In the manufacture of oxygenated organic acids, the steps consisting of passing a mixture of hydrocarbon and oxygen containing constituents in gaseous phase at a reactive temperature in contact with a catalyst containing compounds of a plurality of metals, one of which belongs to the high-melting-point electronegative low-atomic-volume class, and interadjusting the variable factors to produce a predominance of organic acids.

78. In the manufacture of oxygenated organic acids, the steps consisting of passing a mixture of hydrocarbon and oxygen containing constituents in gaseous phase at a reactive temperature in contact with a catalyst containing compounds of a plurality of metals, two of which belongs to the high-melting-point electronegative low-atomic volume class and interadjusting the variable factors to produce a predominance of organic acids.

79. In the process of making intermediate oxidation products, the steps consisting of passing a gaseous mixture of hydrocarbon and oxygen containing constituents through a hot reactive zone at a temperature below that of continuous self-sustained combustion and interadjusting the variable factors to produce intermediate partial oxidation products with a predominance of organic acids.

80. In the process of making intermediate oxidation products, the steps consisting of passing a gaseous mixture of hydrocarbon and oxygen containing constituents through a hot reactive zone at a temperature below that of continuous self-sustained combustion and interadjusting the variable factors to produce unconsumed oxygen in the tail gas and give intermediate partial oxidation products with a predominance of organic acid.

81. In the manufacture of partial oxidation products, the steps consisting of passing a mixture of carbon-hydrogen-oxygen containing constituents in gaseous phase in contact with a catalyst at an elevated temperature below a red heat and at a pressure less than 5 atmospheres and interadjusting the factors to produce a predominance of organic acids.

82. In the manufacture of partial oxidation products, the steps consisting of passing a mixture of carbon-hydrogen-oxygen containing constituents in gaseous phase in contact with a catalyst containing compounds of at least two groups of the periodic series other than the alkali metal group and interadjusting the factors to produce a predominance of organic acids.

83. In the manufacture of partial oxidation products, the steps consisting of passing a mixture of carbon-hydrogen-oxygen containing constituents in gaseous phase in contact with a catalyst containing compounds of at least two groups of the periodic series other than the alkali metal groups at an elevated temperature below that of continuous self-sustained combustion and at a pressure of less than 5 atmospheres and interadjusting the factors to produce a predominance of organic acids.

84. In the manufacture of a liquid partial oxidation product having a plurality of different hydrocarbons containing artificially-introduced chemically-combined oxygen, the steps consisting of forming a gaseous phase mixture of hydrocarbon and oxygen and passing the mixture over a catalyst at a reactive temperature below that of continuous self-sustained complete combustion, and interadjusting the factors to produce a predominance of organic acids in the product.

85. In the manufacture of a liquid partial oxidation product having a plurality of different hydrocarbons containing artificially-introduced chemically-combined oxygen, the steps consisting of forming a gaseous phase mixture of hydro-carbon and oxygen and passing the mixture over a catalyst at a reactive temperature below a red heat, and interadjusting the factors to produce intermediate oxidation products with a predominance of acids.

86. In the manufacture of a liquid partial oxidation product having a plurality of different hydrocarbons containing artificially-introduced chemically-combined oxygen, the steps consisting of forming a vapor phase mixture of hydrocarbon and oxygen and passing the mixture over a catalyst at a reactive temperature below a red heat, and interadjusting the factors to produce intermediate oxidation products with a predominance of acids.

87. As a new article of manufacture, a liquid partial combustion product containing a material proportion of aldehyde fatty acids.

88. As a new article of manufacture, a liquid partial combustion product containing a material proportion of intermediate oxidation products with a preponderance of fatty acids.

89. As a new article of manufacture, a liquid partial combustion product containing at least twenty percent of aldehyde fatty acids.

90. As a new article of manufacture, a liquid partial combustion product containing at least thirty-three and one-third percent of intermediate oxidation products, including a predominance of aldehyde fatty acids.

91. As a new article of manufacture, a liquid partial oxidation product containing oxygen derivatives of hydrocarbons of different molecular weights and containing a preponderance of oxygenated organic acids.

In testimony whereof I have hereunto set my hand.

JOSEPH HIDY JAMES.